(12) United States Patent
Choi et al.

(10) Patent No.: US 6,242,596 B1
(45) Date of Patent: Jun. 5, 2001

(54) PREPARATION OF BETAMETHYL CARBAPENEM INTERMEDIATES

(75) Inventors: Woo-Baeg Choi, North Brunswick; Guy R. Humphrey, Belle Mead; Paul J. Reider; Ichiro Shinkai, both of Westfield; Andrew S. Thompson, Mountainside; Ralph P. Volante, Cranberry, all of NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 08/241,958

(22) Filed: May 12, 1994

Related U.S. Application Data

(63) Continuation of application No. 07/947,186, filed on Sep. 18, 1992, now abandoned.

(51) Int. Cl.[7] ............... C07D 205/08; C07D 405/04; C07F 7/18

(52) U.S. Cl. .......................................................... 540/200

(58) Field of Search ......................... 500/200; 540/200

(56) References Cited

U.S. PATENT DOCUMENTS

| 4,576,746 | * | 3/1986 | Favara | 540/200 |
| 4,801,719 | * | 1/1989 | Oertle | 540/200 |
| 4,960,880 | * | 10/1990 | Vyeo | 540/200 |
| 4,992,545 | * | 2/1991 | Hall | 540/200 |
| 5,574,152 | * | 11/1996 | Miura | 540/200 |

FOREIGN PATENT DOCUMENTS

| 0 052 299 | 5/1982 | (EP) . |
| 0 300 657 | 3/1993 | (EP) . |
| 0 546 742 | 6/1993 | (EP) . |

OTHER PUBLICATIONS

Kametani, T. *Heterocycles* 17: 463–506 (1982).
Stibata Tetrahedron Letters, vol. 26, No. 39, pp. 4739–4742, 1985.
Nagao J. Am. Chem. Soc. 1986, 108, 4673–4675.
Iimori Tetrahedron Letters, vol. 27, No. 19, pp 2149–2152, 1986.
Kawabata Tetrahedron Letters, vol. 27, No. 51, pp 6241–6244, 1986.
Endo Can. J. Chem. 65, 2140 (1987).
Ohta J. Org. Chem. 1987, 52, 3174–3176.
Fuentes J. Org. Chem. 1987, 52, 2563–2567.

(List continued on next page.)

*Primary Examiner*—Mark L. Berch
(74) *Attorney, Agent, or Firm*—Sylvia A. Ayler; Mark R. Daniel

(57) ABSTRACT

A process for making a beta methyl carbapenem intermediate is disclosed. A compound of formula I:

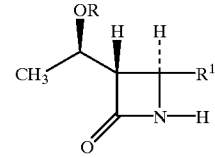

is contacted in a non-reactive solvent with methyl Meldrum's acid and a base to produce a compound of formula III:

III

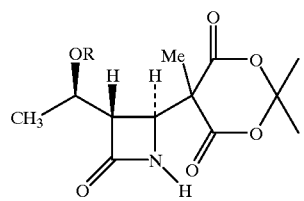

Compound III is treated in an aprotic solvent with a scavenging base, an alkali metal halide and a tri-organo silyl protecting compound for nitrogen to produce a compound of formula IV:

IV

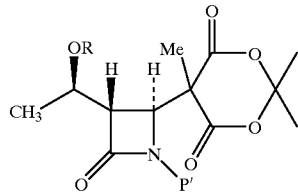

Compound IV may be reacted with a nucleophile Nu—X in a non-reactive solvent and base, and the mixture acidified to produce a compound of formula V.

V

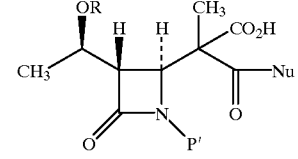

Compound V may be reacted with mild acid to produce a compound of formula VI.

VI

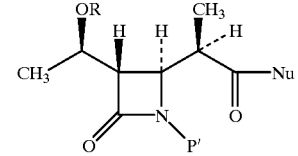

10 Claims, No Drawings

OTHER PUBLICATIONS

Hatanaka Tetrahedron Letters, vol. 28, No. 1, pp 83–86, 1987.
Kim Tetrahedron Letters, vol. 28, No. 5, pp 507–510, 1987.
Prisad Tetrahedron Letters, vol. 28, No. 17, pp 1857–1860, 1987.
Ito Tetrahedron Letters, vol. 28, No. 52, pp 6625–6628, 1987.
Endo Can. J. Chem. 66, 1400 (1988).
Martel Can. J. Chem. vol. 66, 1537 (1988).
Ni J. Org. Chem. 1988, 53, 2129–2132.
Sownv J. Org. Chem. 1988, 53, 4154–4156.
Kawabata Tetrahedron vol. 44, No. 8, pp 2149–2165, 1988.
Deziel Tetrahedron Letters, vol. 29, No. 1, pp 61–64, 1988.
Bayless Tetrahedron Letters, vol. 29, No. 48, pp 6345–6348, 1988.
Shirai Chemistry Letters, pp 445–448, 1989.
Udodong J. Org. Chem. 1989, 54, 2103–2112.
Kaga Tetrahedron Letters, vol. 30, No. 1 pp 113–116, 1989.
Rao Tetrahedron Letters, vol. 31, No. 2, pp 271–274, 1990.
Kijamura Tetrahedron Letters, vol. 31, No. 4, pp 549–552, 1990.
Kita Chem. Pharm. Bull. 39(9) 2225–2232, 1991.
Ito Tetrahedron vol. 47, No. 16/17, pp 2801–2820, 1991.
Rao Tetrahedron: Asymmetry vol. 2, No. 4, pp 255–256, 1991.
Uyeo Tetrahedron Letters, vol. 32, No. 19, pp 2143–2144, 1991.
Bender J. Org. Chem. 1992, 57, 2411–2418.
Kobayashi Tetrahedron vol. 48, No. 1, pp 55–56, 1992.
Shirh Tetrahedron Letters, vol. 29, No. 49, pp 6461–6464 (1988).
Goh, Tet. Letters 31, 553(1990).
T. Honda, et al., Chem. Let. No. 4, pp. 531–534 (1990).
Kametani, et al., Hetercycles, vol. 19, No. 6, pp. 1023–1032 (1982).
Heterocycles, vol. 35, No. 1, pp. 139–142 (1993) (Masataka et al).
Barton et al, Tet Letters 32, 2471 (May 1991.*
Hard, J.A.C.S. 76, 5563 (1954).*
Heisig, Org. Syn Coll vol. 3, p. 212.*
Arcadi, SYNLETT 407 (Jun. 1991).*
Vig I, Ind. J. Chem 16B, 449 (1978).*
Vig II, Ind. J. Chem 16B, 114 (1978.*

* cited by examiner

PREPARATION OF BETAMETHYL CARBAPENEM INTERMEDIATES

This application is a continuation of U.S. application Ser. No. 07/947,186, abandoned filed on Sep. 18, 1992, herewith, priority of which is claimed hereunder.

BACKGROUND OF THE INVENTION

A process for making a beta methyl carbapenem intermediate is disclosed. A compound of formula I:

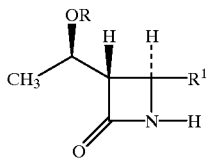

is contacted in a non-reactive solvent with methyl Meldrum's acid and a base to produce a compound of formula III:

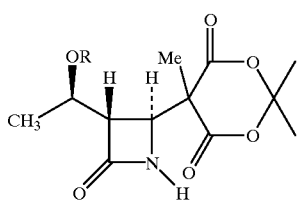

Compound III is treated in an aprotic solvent with a scavenging base, an alkali metal halide and a tri-organo silyl protecting compound for nitrogen to produce a compound of formula IV:

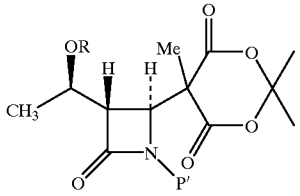

Compound IV may be reacted with a nucleophile Nu—X in a non-reactive solvent and base, and the mixture acidified to produce a compound of formula V.

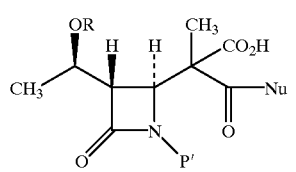

Compound V may be reacted with mild acid to produce a compound of formula VI.

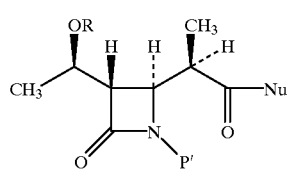

Numerous routes to beta-methyl carbapenem intermediates of formula VI have been cited in the literature:

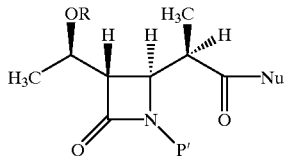

Tetrahedron Letters, Vol. 26, No. 39, pp 4739–4742, 1985; J. Am. Chem. Soc. 1986, 108, 4673–4675; Tetrahedron Letters, Vol. 27, No. 19, pp 2149–2152, 1986; Tetrahedron Letters, Vol. 27, No. 51, pp 6241–6244, 1986; Can. J. Chem 65, 2140 (1987); J. Org. Chem. 1987, 52, 3174–3176; J. Org. Chem. 1987, 52, 2563–2567; J. Org. Chem. 1987, 52, 5491–5492; Tetrahedron Letters, Vol. 28, No. 1, pp 83–86, 1987; Tetrahedron Letters, Vol. 28, No. 5, pp 507–510, 1987; Tetrahedron Letters, Vol. 28, No. 17, pp 1857–1860, 1987; Tetrahedron Letters, Vol. 28, No. 52, pp 6625–6628, 1987; Can. J. Chem. 66, 1400 (1988); Can. J. Chem. Vol. 66, (1988); J. Chem. Soc. Chem. Commun. 1988; J. Org. Chem. 1988, 53, 2131–2132; J. Org. Chem. 1988, 53, 4154–4156; Tetrahedron Vol. 44, No. 8, pp 2149 to 2165, 1988; Tetrahedron Letters, Vol. 29, No. 1, pp 61–64, 1988; Tetrahedron Letters, Vol. 29, No. 49, pp 6461–6464, 1988; Tetrahedron Letters, Vol. 29, No. 48, pp 6345–6348, 1988; Chemistry Letters, pp 445–448, 1989; J. Chem. Soc. Perkin Trans. I 1989; J. Org. Chem. 1989, 54, 2103–2112; Tetrahedron Letters, Vol. 30, No. 1 pp 113–116, 1989; Tetrahedron Letters, Vol. 31, No. 2, pp 271–274, 1990; Tetrahedron Letters, Vol. 31, No. 4, pp 549–552, 1990; Chem. Pharm. Bull. 39(9) 2225–2232 (1991); Tetrahedron Vol. 47, No. 16/17, pp 2801–2820, 1991; Tetrahedron: Asymmetry Vol. 2, No. 4, pp 255–256, 1991; Tetrahedron Letters, Vol. 32, No. 19, pp 2143–2144, 1991; J. Org. Chem. 1992, 57, 2411–2418; Tetrahedron Vol. 48, No. 1, pp 55–66, 1992;

Previous methods to stereoselectively prepare β-methyl carbapenems include:

(1) hydrogenation of a 4-(2-propenyl) substituted azetidinone.

(2) stereoselective protonation of an enolate ion.

(3) reaction of 4-acetoxy azetidinone with a chiral enolate.

These methods required difficult multistep preparation of intermediates (1) and/or reagents (3), tedious manipulation of highly reactive intermediates at low temperature (2), or the use of expensive reagents (2,3).

The invention disclosed herein provides a versatile route to β-methyl intermediates (VI Scheme 1 with high stereoselectivity from readily available starting materials in four steps.

SUMMARY OF THE INVENTION

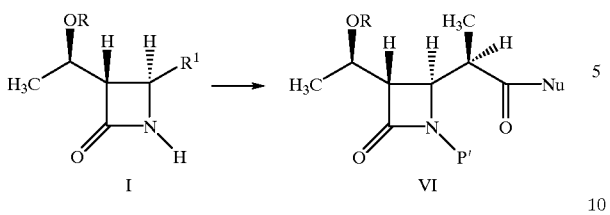

wherein R and P' are protecting groups R¹ is a methylmalonic acid ester and Nu is a nucleophilic group. Process intermediates are also disclosed.

DETAILED DESCRIPTION OF THE INVENTION

In one embodiment, the invention concerns a process of making Beta-methyl carbapenem intermediates of formula VI

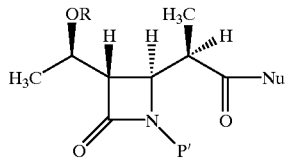

VI wherein
R is
  (a) hydrogen,
  (b) methyl, or
  (c) a hydroxy protecting group such as tri-organo-silyl including tri-$C_{1-4}$ alkyl silyl, phenyl di $C_{1-4}$ alkyl silyl and diphenyl mono $C_{1-4}$ alkyl silyloxy including tert-butyl-dimethylsilyl; and isopropyl dimethyl-silyl and P' is a nitrogen protecting group such as tri-organo-silyl, including tri-$C_{1-4}$ alkylsilyl, phenyl di $C_{1-4}$ alkyl silyl and diphenyl mono $C_{1-4}$ alkyl silyl including tert-butyl-dimethylsilyl; and isopropyldimethyl-silyl; comprising:
  (a) contacting a compound of Formula I

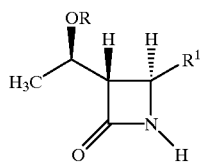

I

R¹ is
  (a) —O—C(O)—R" wherein R" includes $C_{1-6}$ alkyl, allyl and substituted phenyl wherein the substituent is hydrogen, $C_{1-3}$ alkyl, halo, nitro, cyano or $C_{1-3}$ alkyloxy,
  (b) —S(O)$_n$—R² wherein n is 1 or 2, and R² is or an aromatic group such phenyl, biphenyl, naphthyl, said aromatic group optionally substituted with, for example halide, such as chloride or bromide, or $C_{1-4}$ alkyl,
  (c) halo, including Cl and Br in a non-reactive solvent with 2,2,5-trimethyl-1,3-dioxan-4,6-dione and a base to yield a compound of Formula III:

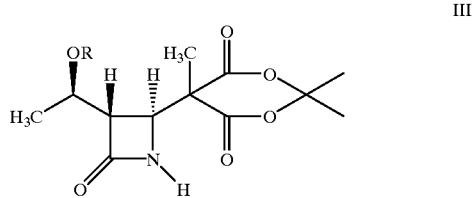

III

For purposes of this specification protecting groups wherein R and P' are intended to include but are not limited to tri-organosilyl as defined above; suitable alternatives are cited in Protecting Groups In Organic Synthesis, Theodora W. Green, John Wiley and Sons 1981.

For purposes of this specification non-reactive solvents are defined to include a broad spectrum of non-reacting solubilizing agents including aromatic solvents such as benzene, toluene and xylene; etheral solvents including diethyl ether, di-n-butyl and diisopentyl ethers, anisole, cyclic ethers such as tetrahydropyran, 4-methyl-1,3-dioxane, dihydropyran, tetrahydrofurfuryl, methyl ether, ethyl ether, furan, 2-ethoxytetrahydrofuran and tetrahydrofuran (THF) ester solvents including ethyl and isopropyl acetate; halo carbon solvents including mono or dihalo $C_{1-4}$ alkyl; alcohols, including $C_{1-6}$ alkanol; and $C_{6-10}$ linear, branched or cyclic hydrocarbon solvents including hexane and toluene; and nitrogen containing solvents including N,N-dimethylacetamide, N,N-dimethylformamide and acetonitrile.

For purposes of this specification bases are intended to include carbonates including alkali carbonates such as $K_2CO_3$ and tertiary $C_{1-4}$ alkyl amines including triethyl amine.

The molar ratio of compound of formula I to methyl Meldrum's acid should be approximately 1 to 1 or greater. The molar ratio of compound of formula I to base should be approximately 0.8–1.2 to 1. The reaction may be conducted from approximately 0 to 60° C. preferably 40 to 50° C. The reaction is allowed to proceed until substantially complete in 1 minute to 20 hours, typically 14 hrs.

(b) contacting a compound of formula III in an aprotic solvent with a scavenging base, an alkali metal halide and a tri- organo halo silane to yield a compound of formula IV

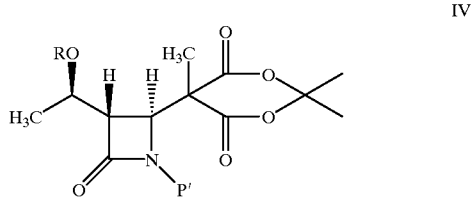

IV

For purposes of this specification, the aprotic solvent is intended to include N,N-di$C_{1-6}$ alkylcarbonylamide such as N,N-dimethyl formamide (DMF), toluene, tetrahydrofuran and dichloromethane. The scavenging base is intended to include pyrrole, pyridine, pyrrolidine, N,N di$C_{1-3}$alkyl amino pyridine such as N,N-dimethyl amino pyridine tri- $C_{1-4}$alkylamine such as triethylamine and imidazole. The alkali metal halide may include sodium, potassium or lithium as the metal, and iodine, bromine, or chlorine as the halide. The tri-organo halo silane is intended to include tri-$C_{1-4}$ alkyl halo silane, such as Butyldimethyl silyl chloride; phenyl di $C_{1-4}$ alkyl halo silane, and diphenyl $C_{1-4}$ alkyl halo silane, wherein halo is intended to include chloride, bromide and iodide. The ratio of formula III to silane should be approximately 1 to 1 or less. The molar ratio of silane to scavenging base should be approximately 1 to 1 or less. The ratio of silane to halide should be approximately 1 to 1 or less.

The reaction is conducted at 0 to 70° C., until essentially complete in 2–72 hours.

(c) contacting a compound of formula IV in a non-reactive solvent or $C_{1-6}$ alkanol with a base and nucleophile of formula NuX to yield after acidification a compound of formula V

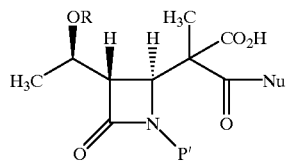
V

The non-reactive solvent is as defined above.

For purposes of this specification $C_{1-6}$ alkanol shall include methyl, ethyl, propyl, isopropyl, butyl and siobutyl alcohol. The base shall include alkali hydroxide such as potassium lithium or sodium hydroxide and shall include alkali carbonate such as sodium or potassium carbonate. Acidification may be accomplished with any suitable acid such as a mineral acid including HCl, $H_2SO_4$ or an organic acid such as acetic or formic acid.

The ratio of formula IV to base should be approximately 1 to 1 or less, and approximately 1 to 2 acid may be used for acidification.

The ratio of formula IV to nucleophile should be approximately 1 to 1 or greater. The reaction is allowed to proceed at −20 to 25° C. until substantially complete in 10 to 100 minutes.

As appreciated by those of skill in the art, the particular nucleophile selected is a non-essential aspect of the invention disclosed herein. Any of a vast array of nucleophile may be selected. For example, Nu X is intended to include alkali metal salts of alkoxides, thiolates and enolates. Thus, X is intended to include Na, K, Li, and Cs. Similarly, Nu is intended to include $R^2O^-$ where hydrogen, $C_{1-6}$alkyl and substituted $C_{1-6}$alkyl and phenyl;

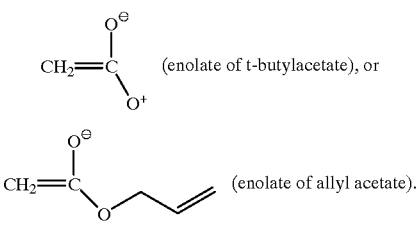

Moreover, with particular regard to $R^2S^-$, $R^2$ is intended to include substituents at position-2 of the carbapenem, as found in commercially available or other active carbapenem antibiotics.

Thus in one aspect applicants anticipates the use of their compounds and process, as illustrated in Schemes 1 and 2, shown below.

As shown in Scheme 1, compound a undergoes a stereoselective decarboxylation to give compound b. Compound b is then converted to active antibiotic as is well-known in the art. See Shih, D. H. et al., Heterocycles 1984, 21, 79. Similarly, as shown in Scheme 2, compound a undergoes a stereoselective decarboxylation to give the thio ketone b' which is converted to active antibiotic as is well known in the art. See Greenlee, et al., Heterocycles 1989, 28, 195 and references therein.

Scheme 1

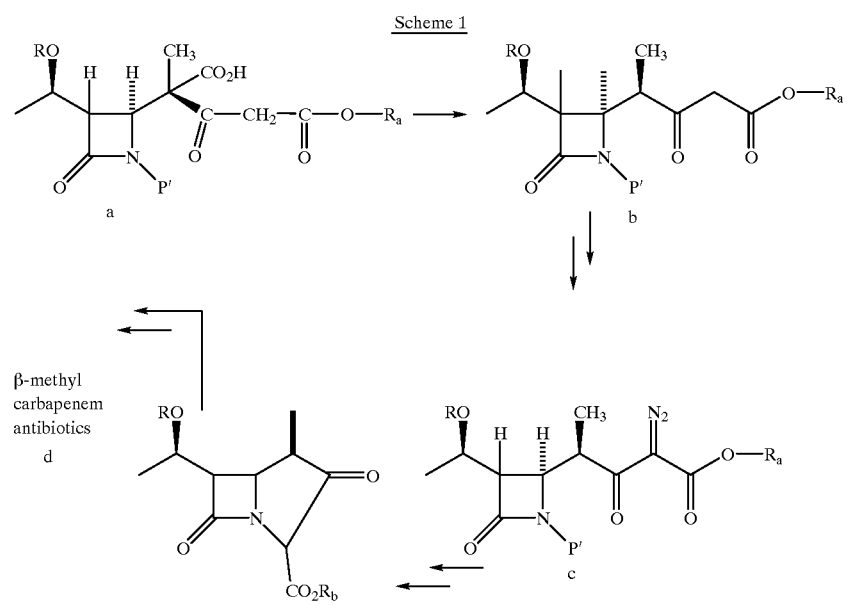

Scheme 2

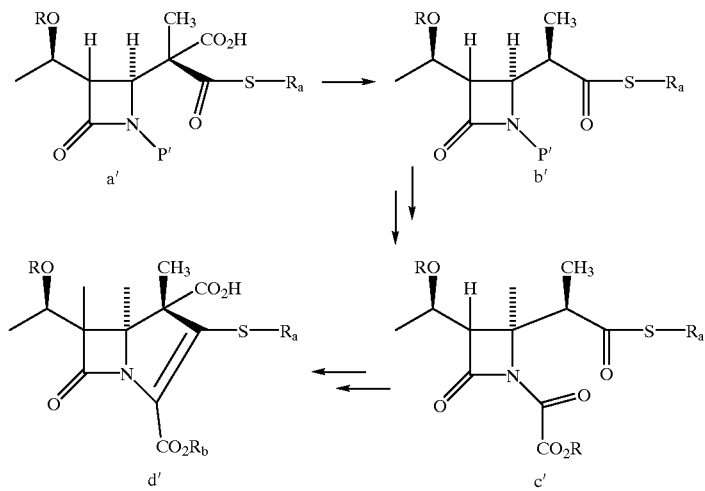

Thus, for purposes of this specification Nu is intended to include, but not be limited to $CH_2CO_2$t-Bu, sulfur or oxygen containing groups —$SR^2$ and —$OR^2$ wherein $R^2$ is selected from the group consisting of hydrogen; straight and branched loweralkyl having from 1 to 10 carbon atoms; alkenyl, alkynyl, having from 2 to 10 carbon atoms; cycloalkyl having from 3 to 6 carbon atoms; cycloalkylalkyl wherein the cycloalkyl moiety comprises 3 to 6 carbon atoms and the alkyl moiety comprises 1 to 10 carbon atoms; alkylcycloalkyl wherein the alkyl moiety comprises 1 to 6 carbon atoms and the cycloalkyl moiety comprises 3 to 6 carbon atoms; aryl such as phenyl and naphthyl; aralkyl such as benzyl, phenethyl and the like; heterocyclyl (saturated and unsaturated) comprising mono- and bicyclic structures having from 5 to 10 ring atoms wherein one or more of the hetero atoms is selected from oxygen, nitrogen or sulphur, such as thiophene, imidazolyl, tetrazolyl, furyl and the like; heterocyclylalkyl which comprises the immediately preceding heterocyclyl moieties and the alkyl moiety comprises from 1 to 10 carbon atoms; the substituent (or substituents) relative to the above-named radicals is selected from the group consisting of amino, hydroxyl, cyano, carboxyl, nitro, chloro, bromo, fluoro, lower alkoxy having from 1 to 6 carbon atoms, mercapto, perhaloloweralkyl such as trifluoromethyl, loweralkylthio, guanidino, amidino, sulfamoyl, and N-substituted; sulfamoyl, amidino and guanidino wherein the N-substituent is loweralkyl having from 1 to 6 carbon atoms or aryl having 6–10 carbon atoms.

To illustrate, the aryl group includes but is not limited to $R^2$ as defined in U.S. Pat. No. 4,962,103, issued Oct. 9, 1990, wherein —$SR^2$ is defined as

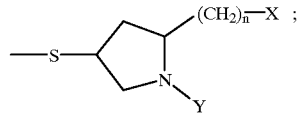

those defined in U.S. Pat. Nos. 4,933,333, 4,943,569, and 5,122,604 wherein —SR2 is defined as

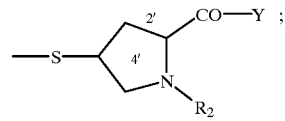

those defined in U.S. Pat. No. 4,866,171 issued Sep. 12, 1989 wherein —$SR^2$ is defined as

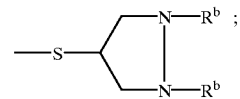

those defined in U.S. Pat. No. 5,034,384, issued Jul. 23, 1991, wherein $R^2$ is

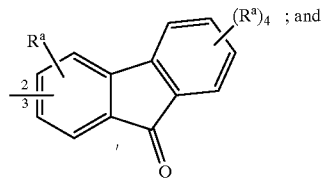

those defined in U.S. Pat. No. 5,011,832 issued Apr. 30, 1991, wherein $R^2$ is

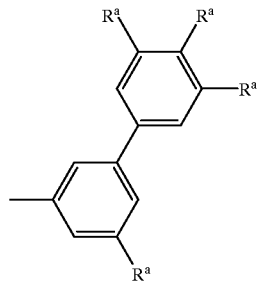

all of which are hereby incorporated by reference. Specific substituted on these aryl groups can be illustrated by the following species disclosed in the above references

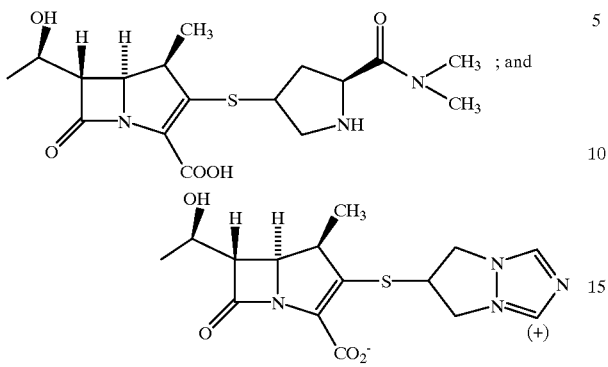

(d) contacting a compound of formula V in an ester or ether solvent with a mild acid to yield a compound of formula VI

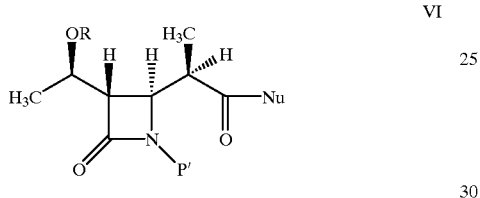

VI

For purposes of this specification, the ester solvent is intended to include ethyl and isopropyl acetate and etheral solvents as defined above including methyl t-butyl ether. Mild acid are intended to include acetic and formic acid. The molar ratio of formula V to acid should be 1 to 1 or greater. The reaction may be allowed to proceed at from 10 to 150° C. until substantially complete in 10 to 120 minutes.

In a second embodiment, the invention concerns intermediate compounds of formulas III, IV and V.

The invention is further detailed in Scheme 3 and the Examples thereafter.

4-acetoxyazetidinone I (Scheme 3) was reacted with methyl Meldrum's acid, II (2,2,5-trimethyl-1,3-dioxan-4,6-dione), giving β-lactam III. Silylation of III with t-butyl dimethylsilylchloride/triethylamine/sodium iodide gave the N-silylated adduct IV. Reaction of IV with a nucleophile gave the carboxylic acid derivative V which underwent stereoselective decarboxylation giving the β-methyl azetidinone VI, a precursor to β-methyl carbapenem antibiotics. Use of intermediate VI is illustrated in Schemes 1 and 2, Supra.

Scheme 3

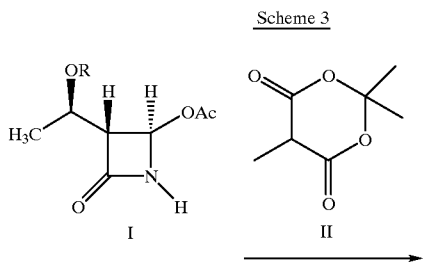

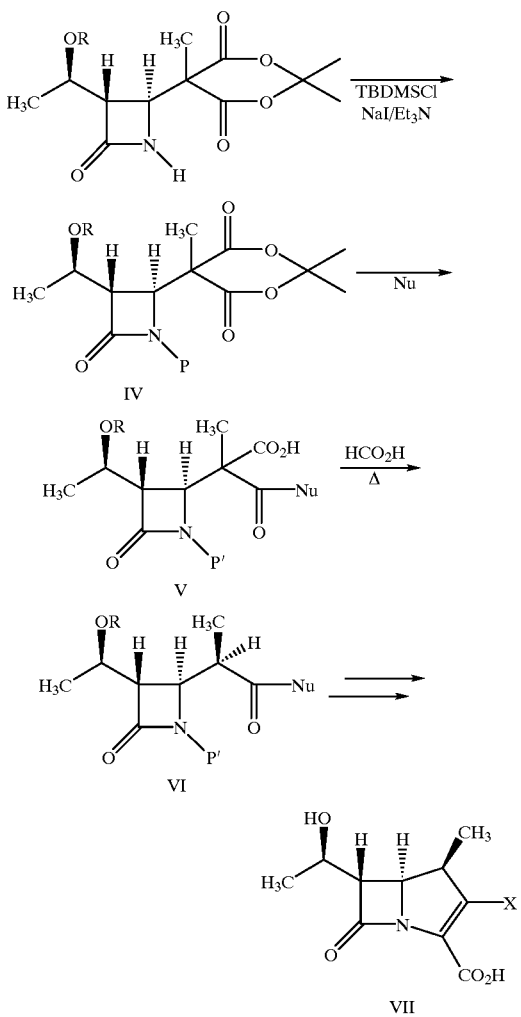

EXAMPLE 1

Preparation of Meldrum's Acid Adduct III 2,2,5-trimethyl-1,3-dioxan-4,6-dione II (17.4 g, 110 mmol), 4-acetoxy-azetidinone I (28.7 g, 100 mmol) and K$_2$CO$_3$ (15.2 g, 110 mmol) were mixed in dry acetonitrile (150 mL, KF=5.6 mg/mL), and the mixture was aged at 45–50° for 14 hours. Upon completion, the reaction mixture was cooled to room temperature and water (150 mL) was added. The organic layer was separated and the aqueous layer was back extracted with acetonitrile (100 mL). Combined organic extracts were washed with brine (100 mL) and concentrated to ca. 50 mL in volume. The mixture was then diluted with heptane (200 mL) and concentrated to 50 mL. Additional heptane (150 mL) was added and the mixture was aged at room temperature for crystallization. The resulting product was collected by filtration, washed with heptane (50 mL) and dried under vacuum at 40–50 for 15 hours to give an off-white crystalline solid (30.9 g, 80.2 mmol). A second crop was obtained by concentrating the combined filtrate and washed to ca. 50 mL in and aging at room temperature to give a white, fluffy solid (2.07 g, 5.4 mmol). Combined yield was 85.6%. Melting Range (° C.) 78–83 d.

$^1$H NMR (in CDCl$_3$) 6.19 (1H, broad, NH), 4.20 (1H, dq, J=3.7 & 6.4 Hz), 4.15 (1H, d, J=2.1 Hz), 3.54 (1H, dd, J=2.1 & 3.7 Hz), 1.77 (3H, s, CH$_3$), 1.73 (3H, s, CH$_3$), 1.62 (3H, s, CH$_3$), 1.17 (3H, d, J=6.4 Hz), 0.85 (9H, s, Si-t-Bu), 0.06

& 0.05 (6H, 2 s, 2 Si—CH$_3$); $^{13}$C NMR (CDCl$_3$) 168.91, 168.51, 167.72, 105.47, 64.70, 61.22, 55.63, 50.99, 30.04, 28.28, 25.78, 22.82, 18.60, 17.95, −4.32, −4.94.

EXAMPLE 2

Preparation of IV

Azetidinone III (7.7 g, 20 mmol) was dissolved in dimethylformamide (100 mL, KF=10 mg/mL) and NaI (6.6 g, 44 mmol), triethylamine (8.4 mL, 60 mmol) and N,N-dimethylaminopyridine (0.25 g, 2 mmol), were added consecutively. The mixture was stirred for 5 minutes and t-butyldimethylsilyl chloride (6.6 g, 44 mmol) was added in one portion. The mixture was stirred for 48 hours at room temperature and 50–60° for 15 hours. Upon completion, the reaction mixture was cooled to room temperature and water (100 mL) was added. The mixture was extracted with hexanes (100 mL×2). The combined extracts were washed with 1 N aqueous HCl solution (100 mL) and water (100 mL) and concentrated to dryness. The resulting oily residue was dissolved in 2-propanol (40 mL) and water (40 mL) was added dropwise. It was seeded and additional water (40 mL) was added dropwise and aged at room temperature for crystallization. The resulting product was collected by filtration and dried under vacuum at 40–50° C. 15 hours to give a pale orange crystalline solid (8.4 g, 16.8 mmol). Yield was 84.1%. Melting Range (° C.) 73–73 d. $^1$H NMR (in CDCl$_3$) 4.32 (1H, d, J=2.2 Hz), 3.96 (1H, dq, J=5.9 & 9.4 Hz), 3.66 (1H, dd, J=2.2 & 9.4 Hz), 1.79 (6H, s, 2 CH$_3$), 1.71 (3H, s, CH$_3$), 1.34 (3H, d, J=5.9 Hz), 0.95 & 0.91 (18H, 2 s, 2 Si-t-Bu), 0.25, 0.14, 0.12 & 0.11 (12H, 4 s, 4 Si—CH$_3$); $^{13}$C NMR (CDCl$_3$) 173.72, 168.56, 167.44, 105.43, 68.39, 63.13, 60.92, 50.45, 29.80, 28.09, 26.67, 25.95, 23.61, 23.03, 19.06, 18.02, −4.09, −4.38, −4.76, −4.90.

EXAMPLE 3

Hydrolysis of Silylated Adduct IV

Adduct IV (2.5 g, 5 mmol) was dissolved in THF (10 mL) and the solution was cooled to 0° C. 1 N Aqueous NaOH solution (10 mL, 10 mmol) was added dropwise while the internal temperature was kept below 5° C. The mixture was aged for 1 hour at 0° C. and additional NaOH solution (2 mL, 2 mmol) was added dropwise. Upon completion, the mixture was acidified with formic acid (1.1 mL, 30 mmol) and extracted with ethyl acetate (40 mL). The solution was used for the next step. The diacid can be isolated by concentration of the solvent followed by crystallization of the resulting solid from a mixture of methanol/water. Melting Range (° C.) 97–99 d. $^1$H NMR (in CDCl$_3$) 4.39 (1H, s), 4.07 (1H, q, J=6.5 Hz), 3.29 (1H, d, J=6.2 Hz), 1.28 (3H, d, J=7.6 Hz), 0.95 & 0.90 (18H, 2 s, 2 Si-t-Bu), 0.28, 0.14 & 0.11 (12H, 3 s, 4 Si—CH$_3$); $^{13}$C NMR (CD$_3$OD) 176.79, 173.78, 67.94, 62.15, 57.81, 27.21, 26.59, 22.31, 20.14, 19.01, 17.71, −3.77, −4.46.

EXAMPLE 4

Methanolysis of Silylated Adduct IV

Adduct IV (1.50 g, 3 mmol) was dissolved in methanol (20 mL) and the solution was cooled to 0° C. K$_2$CO$_3$ (0.86 g, 6.2 mmol) was added in 3 portions and the mixture was aged for 1 hour at room temperature. Upon completion, the mixture was quenched with water (10 mL) followed by aqueous HCl solution (10 mL, 1 N) and extracted with ethyl acetate (20 mL). The organic layer was washed with water (20 mL) and concentrated to dryness to give a white foam (1.18 g, 2.5 mmol) in 80% yield. The foam was further purified by crystallization from a methanol/water mixture to give a white crystalline solid. Melting Range (° C.) 125–135 d. $^1$H NMR (in CDCl$_3$) 8.5 (1H, broad, CO$_2$H), 4.34 (1H, d, J=2.4 Hz), 4.09 (1H, q, J=6.4 Hz), 3.76 (3H, s, OCH$_3$), 3.11 (1H, dd, J=2.4 & 6.8 Hz), 1.50 (3H, s, CH$_3$), 1.22 (3H, d, J=6.2 Hz), 0.96 & 0.89 (18H, 2 s, 2 Si-t-Bu), 0.29, 0.12, 0.09 & 0.08 (12H, 3 s, 4 Si—CH$_3$); $^{13}$C NMR (CDCl$_3$) 174.57, 174.20, 171.26, 67.37, 61.33, 56.88, 56.54, 53.05, 26.54, 26.02, 22.52, 19.32, 18.34, 18.12, −3.99, −4.43, −4.60, −4.74.

EXAMPLE 5

Decarboxylation of the Diacid V

From the base hydrolysis step, the diacid in ethyl acetate was refluxed with additional formic acid (1.10 mL, 30 mmol) for 2 hours. Aliquot assay showed a mixture of 95:5 ratio of β:α methyl product VI. The mixture was cooled to room temperature and concentrated to an oil. The resulting oil was dissolved in aqueous NaOH solution (1 N, 10 mL, 10 mmol) and aged for 2 hours at room temperature. The solution was acidified with aqueous HCl solution (1 N, 15 mL, 15 mmol) and extracted with ethyl acetate (30 mL). The extract was washed with water and concentrated to ca. 5 mL in volume. To it was added hexanes (60 mL) and aged at room temperature. A white crystalline solid was collected by filtration followed by washing with hexanes (10 mL) to give pure β-methyl formula VII (0.96 g, 3.18 mmol). Overall yield from intermediate IV is 64%. Melting Range (° C.) 144–146 d.

What is claimed is:

1. A process of making a carbapenem intermediate of formula VI:

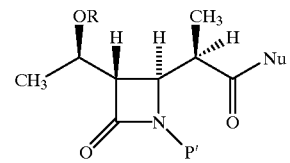

wherein

R is
(a) hydrogen,
(b) methyl, or
(c) a hydroxy protecting group;

P' is a nitrogen protecting group and Nu represents a nucleophilic group comprising:
contacting a compound of formula V:

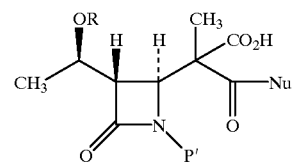

in an ester or ethereal solvent with a mild acid to yield a compound of formula VI:

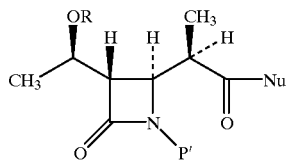

2. A process according to claim 1 further comprising (c) contacting a compound of formula IV

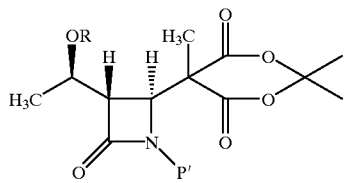

in non-reactive solvent or $C_{1-6}$ alkanol solvent with a base and a nucleophile to yield, after acidification, a compound of formula V

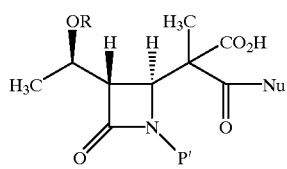

3. A process according to claim 2 further comprising contacting a compound of formula III

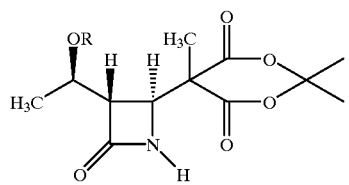

in an aprotic solvent with a scavenging base, an alkali metal halide and a tri-organo halo silane to yield a compound of formula IV

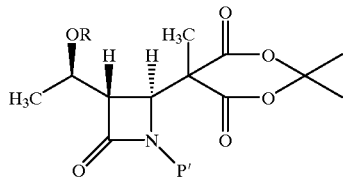

4. A process of making a beta-methyl carbapenem intermediate of formula VI:

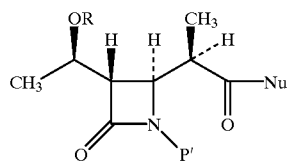

wherein

R is
   (a) hydrogen,
   (b) methyl, or
   (c) a hydroxy protecting group;

P' is a nitrogen protecting group, and Nu is a nucleophilic group comprising:
   (a) contacting a compound of Formula I:

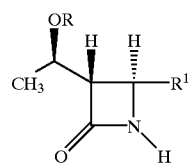

wherein:

$R^1$ is selected from the group consisting of:
   (a) —OC(O)—R" wherein R" is selected from $C_{1-6}$ alkyl, allyl and substituted phenyl wherein the substituent is hydrogen, $C_{1-3}$ alkyl, halo, nitro, cyano or $C_{1-3}$ alkyloxy,
   (b) —S(O)$_n$—$R^2$ wherein n is 1 or 2, and $R^2$ is phenyl, biphenyl, naphthyl, optionally substituted with halide or $C_{1-4}$ alkyl, and
   (c) halo, in a non-reactive solvent with 2,2,5-trimethyl-1,3-dioxan-4,6-dione and a base to yield a compound of Formula III:

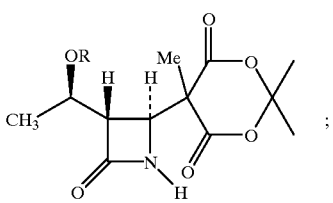

(b) contacting a compound of formula II in an aprotic solvent with a scavenging base, an alkali halide and a tri-organo halosilane to yield a compound of formula IV:

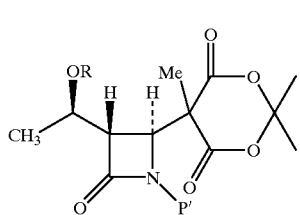

IV wherein P' represents a tri-organosilyl protecting group;
(c) contacting a compound of formula IV in a non-reactive solvent or $C_{1-6}$ alkanol with a base and a nucleophile represented by the formula Nu-X wherein Nu is a nucleophilic group and X is a leaving group,
(d) acidifying to produce a compound of formula V:

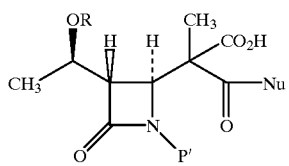

V (e) contacting compound V with a mild acid in an ester or ether solvent to produce a compound of formula VI.

5. A process of making a carbapenem intermediate of formula V:

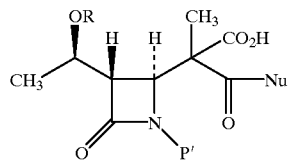

V wherein:
R is
  (a) hydrogen,
  (b) methyl, or
  (c) a tri-organosilyl protecting group for hydroxy selected from tri-$C_{1-4}$ alkylsilyl, phenyl di-$C_{1-4}$ alkylsilyl and diphenyl mono $C_{1-4}$ alkylsilyl;
P' is a tri-organo silyl protecting group for N, selected from tri-$C_{1-4}$ alkylsilyl, phenyl-di $C_{1-4}$ alkylsilyl and diphenyl mono $C_{1-4}$ alkylsilyl, comprising:
contacting a compound of formula IV:

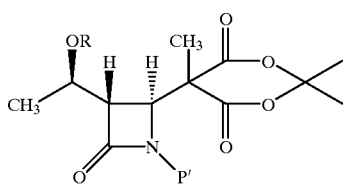

IV in a non-reactive solvent or $C_{1-6}$ alkanol with a base and a compound of formula NuX wherein Nu is a nucleophilic group and X is a leaving group, to yield after acidification a compound of formula V:

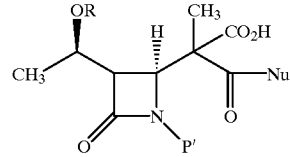

V

6. A process of producing a compound of the formula III:

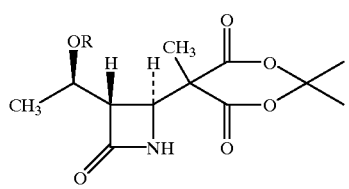

III wherein R represents H, methyl or a hydroxyl protecting group, comprising reacting a compound of formula I:

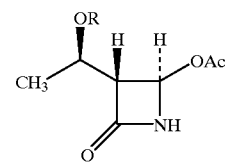

I with a compound of formula II:

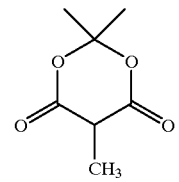

II to produce compound III.

7. A process in accordance with claim 6 wherein the reaction is conducted in dry acetonitrile.

8. A process of making a carbapenem intermediate of formula

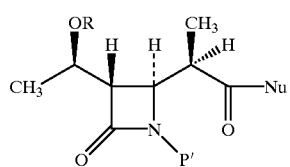

VI in accordance with claim 1 wherein compound V:

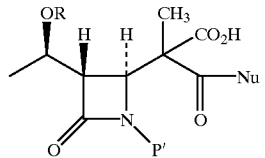 V is contacted with mild acid to yield a 95:5 ratio of β-methyl:α-methyl product.

9. A process in accordance with claim 1 wherein the mild acid is comprised of acetic acid or formic acid.

10. A process in accordance with claim 1 wherein Nu represents a nucleophilic group selected from: —$CH_2CO_2$-t-Bu, —$SR^2$ and —$OR^2$ where $R^2$ is selected from H;

straight and branched $C_{1-10}$ lower alkyl, straight and branched $C_{2-10}$ alkenyl and alkynyl;

$C_{3-6}$ cycloalkyl;

$C_{3-6}$ cycloalkyl-$C_{1-10}$-alkyl;

$C_{1-6}$ alkyl-$C_{3-6}$-cycloalkyl;

aryl;

aralkyl;

heterocyclyl, and heterocyclyl-$C_{1-10}$ alkyl.

* * * * *